United States Patent [19]
Place

[11] Patent Number: 5,403,830
[45] Date of Patent: Apr. 4, 1995

[54] COMPOSITIONS AND METHODS OF TREATING GASTROINTESTINAL DISORDERS

[75] Inventor: Geoffrey Place, Cincinnati, Ohio

[73] Assignee: The Proctor & Gamble Company, Cincinnati, Ohio

[21] Appl. No.: 821,244

[22] Filed: Jan. 10, 1992

Related U.S. Application Data

[63] Continuation of Ser. No. 426,486, Oct. 23, 1989, abandoned, which is a continuation of Ser. No. 23,597, Mar. 9, 1987, abandoned.

[51] Int. Cl.$^6$ .................. A61K 31/415; A61K 31/345; A61K 33/24
[52] U.S. Cl. .................... 514/184; 514/188; 514/272; 514/331; 514/362; 514/370; 514/400; 514/471; 424/653
[58] Field of Search .............. 514/400, 184, 272, 331, 514/362, 370, 471; 424/653; 549/206, 495

[56] References Cited

U.S. PATENT DOCUMENTS

| | | | |
|---|---|---|---|
| 4,148,912 | 4/1979 | Vincent et al. | 424/295 |
| 4,959,384 | 9/1990 | Kraft et al. | 514/390 |
| 5,008,256 | 4/1991 | Clitherow | 514/184 |

FOREIGN PATENT DOCUMENTS

| | | |
|---|---|---|
| 206625 | 12/1986 | European Pat. Off. . |
| 206626 | 12/1986 | European Pat. Off. . |
| 206627 | 12/1986 | European Pat. Off. . |
| 219912 | 4/1987 | European Pat. Off. . |
| 282131 | 9/1988 | European Pat. Off. . |
| 282132 | 9/1988 | European Pat. Off. . |
| 2054373 | 2/1981 | United Kingdom . |
| 86/05981 | 10/1986 | WIPO . |

OTHER PUBLICATIONS

Ward et al., "A Double Blind Trial of the Treatment of Gastric Ulcers with a Combination of DeNol and Cimetidine", Adelaide Scientific Meeting, 1979, Programme Abstracts of Papers, Australian Mineral Foundation, Oct. 8–9; p. A30.
Deutsche Med. Wochenschrift, vol. 112, No. 37, Sep. 1987, pp. 1407–1411.
Wiener Klinische Wochenschrift, vol. 99, No. 14, 17 Jul. 1987, pp. 493–497.
Chemical Abstracts, vol. 107, No. 5, 34d Aug. 1987, p. 397, Abstract No. 36471w.
Goldenberg et al., "Protective Effect of Pepto-Bismol Liquid on the Gastric Mucosa of Rats", Gastroenterology, 69(3), pp. 636–640 (1975).
Vantrappen et al., "Randomized Open Controlled Trial of Colloidal Bismuth Subcitrate Tablets and Cimetidine in the Treatment of Duodenal Ulcers", Gut, 21(4), pp. 329–333 (1980).
Wieriks et al., "Pharmacological Properties of Colloidal Bismuth Subcitrate (CBS, DE-NOL$^R$)", Scand. J. Gastroenterol., 17, Supplement 80, pp. 11–16 (1982).
Koo et al., "Selective Coating of Gastric Ulcer by Tripotassium Dicitrato Bismuthate in the Rat", Gastroenterology, 82, pp. 864–870 (1982).
Lu et al., "Effect of Furaxon and its Analogs on Gastrointestinal Propulsion in Mice", Beijing Yixueyuan Xuebao, 15, pp. 185–187 (1983).
Marshall et al., "Unidentified Curved Bacilli in the Stomach of Patients with Gastritis and Peptic Ulceration", Lancet, 1, pp. 1311–1315 (Jun. 16, 1984).

(List continued on next page.)

Primary Examiner—Richard L. Raymond
Attorney, Agent, or Firm—Kim William Zerby; Douglas C. Mohl; Jacobus C. Rasser

[57] ABSTRACT

The present invention relates to pharmaceutical compositions useful for treating or preventing gastrointestinal disorders. These compositions comprise a bismuth-containing agent, preferably a campylobacter-inhibiting bismuth-containing agent such as bismuth subsalicylate and bismuth subcitrate, and a histamine-2 receptor blocking anti-secretory agent such as cimetidine.

The present invention further relates to methods for treating or preventing gastrointestinal disorders in humans or lower animals by administering a bismuth-containing agent and a histamine-2 receptor blocking anti-secretory agent.

37 Claims, No Drawings

OTHER PUBLICATIONS

McLean et al., "Microbes, Peptic Ulcer and Relapse Rates with Different Drugs", *Lancet*, 2, pp. 525–526 (Sep. 1, 1984).

Hislop et al., "Histological Improvement of Active Chronic Gastritis in Patients Treated with De-Nol", *Australia and New Zealand Journal of Medicine*, 14, p. 907 (1984).

Lam et al., "Randomised Crossover Trial of Tripotassium Dicitrato Bismuthate Versus High Dose Cimetidine for Duodenal Ulcers Resistant to Standard Dose of Cimetidine", *Gut*, 25, pp. 703–706 (1984).

Zeng Zhi-Tian et al., "Double-Blind Short-Term Trial of Furazolidone in Peptic Ulcer", *Lancet*, 1, pp. 1048–1049 (May 4, 1985).

Piper, "Bacteria, Gastritis, Acid Hyposecretion and Peptic Ulcer", *The Medical Journal of Australia*, 142, p. 431 (1985).

Pinkard et al., "Campylobacter-Like Organisms From the Human Stomach-Detection, Characterization, and in Vitro Susceptibilities", Campylobacter III (Pearson et al., editors; 1985), 171–172.

Goodwin et al., "The Association of Campylobacter Pyloridis with Gastritis, and Its In Vitro Sensitivity to Antibiotics and Anti-Ulcer Agents", *Australia and New Zealand Journal of Medicine*, 15 (1 Supplement 1), p. 153 (1985).

Lambert et al., "Campylobacter-Like Organisms (CLO)—In Vivo and In Vitro Susceptibility to Antimicrobial and Anti-Ulcer Therapy", *Gastroenterology*, 88, p. 1462 (1985).

McNulty et al., "Successful Therapy of Campylobacter Pyloridis Gastritis", *Gastroenterology*, 90, p. 1547 (1986).

Goodwin et al., "The Minimum Inhibitory and Bactericidal Concentrations of Antibiotics and Anti-Ulcer Agents Against Campylobacter Pyloridis", *Journal of Antimicrobial Chemotherapy*, 17, pp. 309–314 (1986).

Hirschl et al., "Sensitivity of Campylobacter Pyloridis to Antimicrobials and Anti-Ulcer Drugs", *Z. Antimikrob Antineoplast. Chemother.*, 4 (2), pp. 45–49 (1986).

Salmon, "Combination Treatment: Colloidal Bismuth Subcitrate with $H_2$-Antagonist", *Digestion*, 37, pp. 42–46 (1987).

"Notice of Opposition Against a European Patent", European Patent No. 282,132, by Opponent SmithKline Beecham pic. (Jun. 28, 1993).

"Notice of Opposition", European Patent No. 282,132, by Opponent Glaxo Group Limited, (Jul. 7, 1993).

Peterson et al., *Gastroenterology*, 1979, 77, 1015–1020.

Martin et al., *The Lancet*, 1981, 7–10.

*Digestion*, vol. 37, Supplement 2, Jun. 1987.

*Gut*, 1984, 25, pp. 697–702.

*Pharmac. Ther.*, 1984, 26, pp. 221–234.

Letter by M. C. Brooks dated 11 Jun. 1991, during examination of European Patent No. 206,626.

Letter by J. L'Helgoualch dated 8 Dec. 1992, during examination of European Patent Application No. 88200396.5, Publication No. 282,131.

COMPOSITIONS AND METHODS OF TREATING GASTROINTESTINAL DISORDERS

This is a continuation of application Ser. No. 426,486, filed Oct. 23, 1989, now abandoned, which is a continuation of application Ser. No. 023,597, filed on Mar. 9, 1987, now abandoned.

The present invention relates to pharmaceutical compositions useful for treating or preventing gastrointestinal disorders. These compositions comprise a bismuth-containing agent and a histamine-2 receptor blocking anti-secretory agent. The present invention further relates to methods for treating or preventing gastrointestinal disorders in humans or lower animals by administering a bismuth-containing agent and a histamine-2 receptor blocking anti-secretory agent. These methods may involve either concurrent or non-concurrent administration of the bismuth-containing agent and the histamine-2 receptor blocking anti-secretory agent. These methods may involve either concurrent or non-current administration of the campylobacter-inhibiting antimicrobial agent and the histamine-2 receptor blocking anti-secretory agent.

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental, and psychogenic factors. Accordingly, the diagnosis and management of these disorders can be exceptionally difficult. A detailed discussion of gastrointestinal tract functions, disorders, causes, and treatments can be found in Spiro, *Clinical Gastroenterology* (3d. edition 1983).

Among the chronic disorders of the upper gastrointestinal tract are those which fall under the general categories of gastritis and peptic ulcer disease. Gastritis is, by definition, typified by an inflammation of the stomach mucosa. In practice, though, the disorder is manifested by a broad range of poorly-defined, and heretofore inadequately treated, symptoms such as indigestion, "heart burn", dyspepsia and excessive eructation. A general discussion of gastritis appears in B. J. Marshall and J. R. Warren, "Unidentified Curved Bacilli in the Stomach of Patients with Gastritis and Peptic Ulceration", *The Lancet*, (1984), pp. 1311–1315, and in R. Greenlaw, et al., "Gastroduodenitis, A Broader Concept of Peptic Ulcer Disease", *Digestive Diseases and Sciences*, Vol. 25 (1980), pp. 660–672.

Peptic ulcers are lesions of the gastrointestinal tract lining, characterized by loss of tissue due to the action of digestive acids and pepsin. It has been generally held that peptic ulcers are caused either by gastric hypersecretion, or (more often) by decreased resistance of the gastric lining to digestive acids and pepsin. The medical literature is replete with methods for treating ulcers, including modification of the diet, surgical removal of the lesions, and the use of drugs. Such drugs include: antacids, which serve to counteract excess gastric secretions; anticholinergics, which reduce acid secretion; H$_2$ antagonists, which also block the release of gastric acids; prostaglandins, which increase the resistance of the gastric lining to digestive fluids, and may also inhibit acid secretion; prokinetic agents, which enhance gastrointestinal tract motility; and compositions which form protective barriers over gastric lesions. Prescription and non-prescription drug therapies are generally described in Garnet, "Antacid Products", *Handbook of Non-prescription Drugs*, 7th edition (1982), Chapter 3.

Regardless of the particular drug composition used in treating gastrointestinal disorders, such as gastritis or peptic ulcer disease, the treatment is often imprecise and incomplete. Actual "cures", i.e., successful treatment resulting in total remission of disease, are very often not effected. See A. J. McLean, et al., "Cyto-protective Agents and Ulcer Relapse", 142 *The Medical Journal of Australia*, Special Supplement S25–S28 (1985). Furthermore, many conventional treatments may render subject hypochlorhydric (i.e., with low levels of hydrochloric acid in the stomach) which may predispose them to other disorders, e.g., gastrointestinal infection, halitosis, and gastric carcinomas.

The treatment and prophylaxis of gastrointestinal disorders with bismuth-containing agents is well-known in the art. For example, bismuth subsalicylate (the active ingredient in Pepto-Bismol ®, sold by The Procter & Gamble Company) has demonstrated utility for protecting against ulcer formation (*Gastroenterology*, 69, pp. 636–640 (1975)). Also, bismuth subcitrate (the active ingredient in DeNol ®, sold by Gist-Brocades, N.V.) has been reported to be effective for treating ulcers (*Gut*, 21, pp. 329–333 (1980)). In addition, bismuth subcitrate (*Aust. and N.Z. J. of Medicine*, 14, p. 907 (1984)) and bismuth subsalicylate (*Gastroenterology*, 90, p. 1547 (1986)) have been used to treat gastritis in patients having *Campylobacter pyloridis* infection.

The treatment of gastrointestinal disorders with histamine-2 (hereinafter "H$_2$") receptor blocking anti-secretory agents is also well-known in the art. For example, cimetidine (marketed under the tradename Tagamet ®; Smith Kline & French Laboratories, Philadelphia, Pa.) is an H$_2$ receptor block anti-secretory agent widely used in the treatment of gastric ulcers. This compound, as well as others of this type, are thought to act by blocking the histamine receptors within the stomach mucosa (labeled H$_2$ receptors, to distinguish from those histamine receptors generally associated with allergic response) thereby preventing histamine molecules from signaling the stomach cells to secrete acid. H$_2$ receptor blocking agents which are either more potent and/or longer acting than cimetidine (e.g., ranitidine) are also well-known. (See *C & E News*, Apr. 12, 1982, pp. 24–26). However, while H$_2$ receptor blocking anti-secretory agents have demonstrated effectiveness in treating gastrointestinal disorders and therefore are widely prescribed for this purpose, their utility is questioned in light of the poor long-term outcomes associated with their use (e.g., high relapse rate associated with cimetidine treatment of gastric ulcers; see *The Lancet*, Sep. 1, 1984, pp. 525–526).

Recent research has noted an association between gastritis, peptic ulceration, and the presence of *Campylobacter pyloridis* and campylobacter-like organisims (*The Lancet*, Jun. 16, 1984, pages 1311–1315). This has led to speculation that the high relapse rate observed when treating ulcers with cimetidine is the result of cimetidine allowing healing but adversely affecting the subsequent ability of the gastrointestinal tract to resist ulcerogenic activity of a pathogenic agent (*The Lancet*, Sep. 1, 1984, pages 525–526). However, subsequent research indicates that cimetidine inhibits *Campylobacter pyloridis* growth at low concentrations (*Z. Antimikrob. Antineoplast. Chemother.*, 4 (2), pages 45–49 (1986); *J. Antimicrob. Chemother.*, 17 (3), pages 309–314 (1986)). Furthermore, preliminary findings support the concept that campylobacter-like organisms are not important in the etiology of duodenal ulcer disease (*Gastroenterology*, 88 (5 part 2), p. 1462 (1985)). Thus, it is currently not clear whether the high relapse rate associated with cimetidine treatment is, in fact, due to an adverse affect on the ability of the gastrointestinal tract to resist pathogenic agents.

Clearly, there remains a continuing need to identify new compositions which are effective for treating and preventing gastrointestinal disorders. The present invention provides such novel pharmaceutical compositions, comprising bismuth-containing agents and $H_2$ receptor blocking anti-secretory agents, useful for treating and preventing gastrointestinal disorders.

While, as noted hereinbefore, $H_2$ receptor blocking anti-secretory agents and bismuth-containing agents are individually known for treating and/or preventing gastrointestinal disorders, conventional wisdom regarding their use would mandate that these agents are not compatible for co-administration as taught by the present invention. This is because current understanding of the mode of action of bismuth-containing agents links the activity of these agents to the ability of the bismuth to precipitate onto the gastrointestinal walls in the low pH (i.e., acidic) environment of the gastrointestinal tract. $H_2$ receptor blocking anti-secretory agents, which are known to neutralize the pH of the gastrointestinal tract, are therefore viewed as counterproductive to effective utilization of bismuth-containing agents. However, contrary to conventional teaching, the unconventional compositions and methods of the present invention combine these two agents into compositions and methods which are effective for treating and preventing gastrointestinal disorders.

It is therefore an object of the present invention to provide novel pharmaceutical compositions comprising bismuth-containing agents and $H_2$ receptor blocking anti-secretory agents. It is a further object to provide improved methods for treating or preventing gastrointestinal disorders in humans or lower animals. An additional object is to provide compositions and methods which have improved ability to treat and prevent gastritis and gastrointestinal ulcers, and to improve the long-term outcomes of ulcer treatments. Finally, an object of the present invention is to reduce the incidence of gastritis following ulcer treatment with $H_2$ receptor blocking anti-secretory agents and/or reduce the ulcer relapse rate observed following ulcer treatment with $H_2$ receptor blocking anti-secretory agents.

These and other objects will become readily apparent from the detailed description which follows.

SUMMARY OF THE INVENTION

The present invention relates to pharmaceutical compositions useful for treating or preventing gastrointestinal disorders. These compositions comprise a bismuth-containing agent, especially a bismuth-containing agent effective for inhibiting campylobacter-like organisims (e.g. bismuth subsalicylate; bismuth subcitrate), and a $H_2$ receptor blocking anti-secretory agent (e.g., cimetidine; ranitidine).

The present invention further relates to methods for treating or preventing gastrointestinal disorders in humans or lower animals. These methods comprise administering to a human or lower animal in need of such treatment or prevention a safe and effective amount of a bismuth-containing agent and a safe and effective amount of a $H_2$ receptor blocking anti-secretory agent.

DETAILED DESCRIPTION OF THE INVENTION

Bismuth-containing Agents

The pharmaceutical compositions of the present invention essentially comprise a bismuth-containing agent, preferably in the form of a pharmaceutically-acceptable salt. Such bismuth-containing agents include, for example, bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention. More preferred are bismuth subcitrate and bismuth subsalicylate, with bismuth subsalicylate most preferred.

These agents are well known in the art, and are commercially-available. Their formulation and use in commercial compositions are also well-known, being sold, for example, as DeNol (bismuth subcitrate; sold by Gist-Brocades, N.V.), Noralac (containing bismuth aluminate, alginic acid, and magnesium carbonate; manufactured by North American Pharmaceuticals), Roter bismuth (containing bismuth subnitrate; sold by Roter Laboratories), Fensobar Polvo (containing bismuth subcarbonate among other materials; manufactured by USV Pharmaceutical Corporation), and Pepto-Bismol (containing bismuth subsalicylate; sold by The Procter & Gamble Company).

Especially preferred for use herein are campylobacter-inhibiting bismuth-containing agents. The term "campylobacter-inhibiting bismuth-containing agent", as used herein, means any naturally-occuring, synthetic or semi-synthetic bismuth-containing compound or composition, or mixture thereof, which is safe for human use as used in the compositions and methods of the present invention, and is effective in killing or substantially inhibiting the growth of campylobacter-like organisms, e.g., *Campylobacter pyloridis*, when used in the compositions and methods of this invention. Such campylobacter-like organisms include those described in J. R. Warren and B. J. Marshall, "Unidentified Curved Bacilli on Gastric Epithelium in Active Chronic Gastritis", *The Lancet*, pp. 1273–1275 (1983), and G. Kasper and N. Dickgiesser, "Isolation from Gastric Epithelium of Campylobacter-like Bacteria that are Distinct from '*Campylobacter pyloridis*'", *The Lancet*, pp. 111–112 (1985), the disclosures of both these references being incorporated herein by reference in their entirety. The effectiveness of bismuth-containing agents to kill or substantially inhibit the growth of campylobacter-like organisms may be demonstrated using the various in vitro or in vivo assays known to those skilled in the art. For example, the effectiveness of the preferred bismuth subcitrate and bismuth subsalicylate for inhibiting campylobacter-like organisms are discussed in Hislop et al., "Histological Improvement of Active Chronic Gastritis in Patients Treated with De-Nol", *Aust. and N.Z. J. of Medicine*, 14, p. 907 (1984); and McNulty et al., "Successful Therapy of *Campylobacter Pyloroids*", *Gastroenterology*, 90, p. 1547 (1986), the disclosures of both these articles being incorporated herein by reference in their entirety.

The pharmaceutical compositions of the present invention typically comprise, by weight, from about 0.1% to about 99.8% of the bismuth-containing agent, preferably from about 0.1% to about 75%, and most preferably from about 1% to about 50%.

H₂ Receptor Blocking Anti-Secretory Agents

In addition to the bismuth-containing agent described hereinbefore, the pharmaceutical compositions of the present invention also comprise an H₂ receptor blocking anti-secretory agent. The H₂ receptor blocking anti-secretory agents useful in the present invention include cimetidine, ranitidine, burimamide, metiamide, tiotidine, and oxmetidine, as well as compounds of the formula:

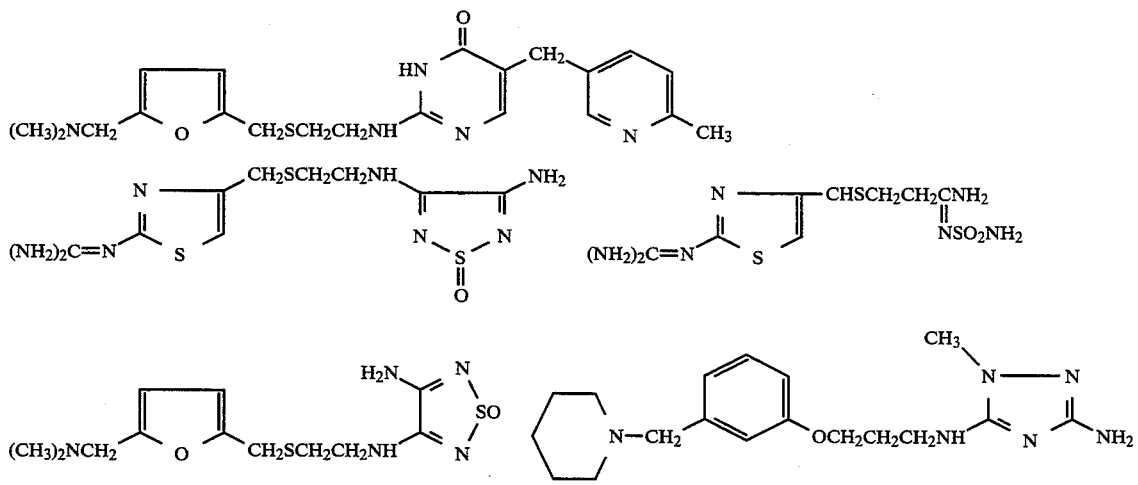

The above structures are well-known in the art (see C & E News, Apr. 12, 1982, pp 24–26, expressly incorporated herein by reference in its entirety). Mixtures of the above H₂ receptor blocking anti-secretory agents may also be employed. The most preferred of these compounds are cimetidine, ranitidine, and mixtures thereof, with cimetidine being especially preferred.

The preparation and use of H₂ receptor blocking anti-secretory agents as described hereinbefore are well-known in the art. For example, the preparation and use of cimetidine are discussed in U.S. Pat. No. 3,950,333, to Durant et al., issued Apr. 13, 1976; Brimblecombe, et al., *J. Int. Med. Res.*, 3, 86 (1975); Brimblecombe, et al., *Brit. J. Pharmacol.*, 53, 435 (1975); and Brogden, et al., *Drugs*, 15, 93–131 (1978); the disclosures of these patents and articles being incorporated herein by reference in their entirety. Also, for example, the preparation and use of ranitidine are discussed in U.S. Pat. No. 4,128,658, to Price et al., issued Dec. 5, 1978; Bradshaw et al., *Brit. J. Pharmacol.*, 66, 464 (1979); Daly, et al., *Gut*, 21, 408 (1980); Berstad, et al., *Scand. J. Gastroenterol.*, 15, 637 (1980); and Wait, et al., *Gut*, 22, 49 (1981); the disclosures of these patents and articles being incorporated herein by reference in their entirety.

The pharmaceutical compositions of the present invention typically comprise, by weight, from about 0.1% to about 99.8% of the H₂ receptor blocking anti-secretory agent, preferably from about 0.1% to about 75%, and most preferably from about 1% to about 50%.

Pharmaceutically-Acceptable Carriers

In addition to the bismuth-containing agent and the H₂ receptor blocking anti-secretory agent as described hereinbefore, the pharmaceutical compositions of the present invention also essentially contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical composition are capable of being commingled with the bismuth-containing agent and the H₂ receptor blocking anti-secretory agent, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

A variety of pharmaceutically-acceptable carriers may be included, depending on the particular dosage form to be used. Various oral dosage forms can be used, including such solid forms as tablets, capsules, granules and bulk powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules and effervescent preparations reconstituted from effervescent granules, containing suitable solvents, preservatives, emulsifying agents, suspending agents, diluents, sweeteners, melting agents, coloring, and flavoring agents. Liquid oral composition typically comprise water and suspending agents, such as magnesium aluminum silicate (e.g., Veegum, manufactured by R. T. Vanderbilt Company, Inc.), as part of the pharmaceutically-acceptable carrier.

Some examples of substances which can serve as pharmaceutically-acceptably carriers are sugars such as lactose, glucose and sucrose; starches such as corn starch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents, excipients, tableting agents, stabilizers, anti-oxidants, and preservatives can also be present. Other compatible pharmaceutical additives and actives (e.g., NSAI drugs; pain killers; muscle relaxants) may be included in the pharmaceutically-acceptable carrier for use in the compositions of the present invention.

Specific examples of pharmaceutically-acceptable carriers that may be used to formulate oral dosage forms of the present invention are described in U.S. Pat. No. 3,903,297, Robert, issued Sep. 2, 1975, incorporated by reference herein in its entirety. Techniques and compositions for making dosage forms useful herein are described in the following references, all incorporated by reference herein in their entirety: 7 *Modern Pharmaceuticals*, Chapters 9 and 10 (Banker and Rhodes, Ed., 1979); Lieberman, et al., *Pharmaceutical Dosage Forms: Tablets* (1981); and Ansel, *Introduction to Pharmaceutical Dosage Forms* (2nd Edition, 1976).

The choice of a pharmaceutically-acceptable carrier to be used in conjunction with the bismuth-containing agent and $H_2$ receptor blocking anti-secretory agent combination of the present invention is basically determined by the way the composition is to be administered. The preferred mode of administering the compositions of the present invention is orally. The preferred unit dosage form is therefore tablets, capsules, and the like, comprising a safe and effective amount of the bismuth-containing agent and the $H_2$ receptor blocking anti-secretory agent combination of the present invention. Pharmaceutically-acceptable carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art.

The pharmaceutically-acceptable carrier employed in conjunction with the bismuth-containing agent and the $H_2$ receptor blocking anti-secretory agent combination of the present invention is used at a concentration sufficient to provide a practical size to dosage relationship. The pharmaceutically-acceptable carriers, in total, may comprise from about 0.1% to about 99.8%, by weight, of the pharmaceutical compositions of the present invention, preferably from about 25% to about 99.8%, and most preferably from about 50% to about 99%.

Methods for Treating or Preventing Gastrointestinal Disorders

Another aspect of the present invention is methods for treating or preventing gastrointestinal disorders. Such methods comprise administering, to a human or lower animal in need of such treatment or prevention, a safe and effective amount of a bismuth-containing agent and safe and effective amount of a $H_2$ receptor blocking anti-secretory agent.

The term "administering", as used herein, refers to any method which, in sound medical practice, delivers the bismuth-containing agent and the $H_2$ receptor blocking anti-secretory agent to the subject to be treated in such a manner so as to be effective in the treatment of the gastrointestinal disorder. Preferably, both these agents are administered orally.

The term "gastrointestinal disorder", as used herein, encompasses any disease or other disorder of the upper gastrointestinal tract of a human or lower animal. The term "upper gastrointestinal tract", as used herein, is defined to include the esophagus, the stomach, the duodenum, and the jejunum. Such gastrointestinal disorders include, for example: disorders not manifested by presence of ulcerations in the gastric mucosa (herein "non-ulcerative gastrointestinal disorders"), including chronic or atrophic gastritis, non-ulcer dyspepsia, esophageal reflux disease and gastric motility disorders; and "peptic ulcer disease", i.e., gastric, duodenal and jejunal ulcers. Gastrointestinal disorder especially refers to such disorders of the upper gastrointestinal tract which are conventionally treated with $H_2$ receptor blocking anti-secretory agents alone.

The phrase "safe and effective amount", as used herein, means an amount of a bismuth-containing agent or $H_2$ receptor blocking anti-secretory agent, when used in combination with each other according to the compositions and methods of the present invention, high enough to significantly positively modify the condition to be treated but low enough to avoid serious side effects (at a reasonable benefit/risk ratio), within the scope of sound medical judgment. The safe and effective amount of the agents of the present invention will vary with the particular condition being treated, the age and physical condition of the patient being treated, the severity of the condition, the duration of treatment, the nature of concurrent therapy, the specific agents employed, the particular pharmaceutically-acceptable carrier utilized, and like factors within the knowledge and expertise of the attending physician.

The methods of the present invention typically involve administering the bismuth-containing agent in an amount of from about 50 mg to about 5000 mg of bismuth per day. (As used herein, the quantity of the bismuth-containing agents to be administered is indicated by the weight of elemental bismuth present in the dose of the bismuth-containing agent. Thus, the actual weight of a dose of a bismuth-containing agent will be greater than the amount of bismuth indicated.) Preferably, from about 500 mg to about 1500 mg of bismuth are administered per day. Most preferably, the bismuth-containing agent is bismuth subcitrate and, especially, bismuth subsalicylate.

The method of the present invention typically involves administering the $H_2$ receptor blocking anti-secretory agent in an amount of from about 1 mg to about 10 g per day. Preferably from about 50 mg to about 5000 mg, more preferably from about 100 mg to about 1500 mg, most preferably from about 400 mg to about 1200 mg, of cimetidine is administered per day.

The methods of the present invention comprise administering the bismuth-containing agent and the $H_2$ receptor blocking anti-secretory agent either concurrently or non-concurrently. The term "concurrently", as used herein, means that the two agents are administered within 24 hours or less of each other, preferably within about 12 hours of each other, more preferably within about 1 hour of each other, and most preferably within about 5 minutes of each other; and includes co-administration of the agents by administering a composition of the present invention. The term "non-concurrently", as used herein, means that the two agents are administered more than 24 hours apart.

The methods of the present invention in which the agents are administered concurrently comprise any dosing regimen in which part or all of the dosing of the agents is preformed concurrently. Thus, for example, methods comprising concurrent dosing of the agents include:

1. 14 days of administration of a pharmaceutical composition of the present invention.
2. 21 days of a regimen wherein the bismuth-containing agent is administered in the morning and the $H_2$ receptor blocking anti-secretory agent is administered at night (approximately 12 hours apart).
3. 28 days of administration of the bismuth-containing agent and the $H_2$ receptor blocking anti-secretory agent essentially simultaneously (i.e., within about 5 minutes of each other), followed by 7 days of treatment with only the bismuth-containing agent.
4. 3 days of administration of only the bismuth-containing agent, followed by 21 days of administration of the bismuth-containing agent and the $H_2$ receptor blocking anti-secretory agent essentially simultaneously (i.e., within about 5 minutes of each other).

The methods of the present invention in which the agents are administered non-concurrently comprise any dosing regimen in which none of the dosing of the agents is performed concurrently. Thus, for example, methods comprising non-concurrent dosing of the agents include:

1. 28 days of alternating daily dosing of the bismuth-containing agent and the $H_2$ receptor blocking anti-secretory agent, starting with the $H_2$ receptor blocking anti-secretory agent and ending with the bismuth-containing agent.
2. 14 days of administration of the $H_2$ receptor blocking anti-secretory agent followed by 14 days of administration of the bismuth-containing agent.
3. 7 days of administration of the bismuth-containing agent, followed by 14 days of administration of the $H_2$ receptor blocking anti-secretory agent.

For the methods of the present invention, the duration of administration of the agents during either concurrent or non-concurrent dosing of the agents will vary according to the specific gastrointestinal disorder being treated, but typically is within the range of from about 1 to about 60 days. In general, however, in methods for treatment of non-ulcerative gastrointestinal disorders the duration of treatment comprises administering the agents for from about 3 to about 21 days. In methods for treatment of peptic ulcer disease, the duration of treatment comprises administering the agents for from about 14 to about 56 days. If the compositions of the present application are administered, similar durations are utilized depending on the gastrointestinal disorder to be treated.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE I

Pharmaceutical Compositions in Tablet Form

Tablets are prepared by conventional methods, such as mixing and direct compaction, formulated as follows:

| Ingredients | Mg per Tablet |
| --- | --- |
| Bismuth subsalicylate | 300 of bismuth |
| Cimetidine | 300 |
| Microcrystalline cellulose | 100 |
| Sodium starch glycolate | 30 |
| Magnesium stearate | 3 |

When one tablet is administered orally 4 times per day for 14 days, the above compositions significantly improve the condition of a patient suffering from gastritis. A significant long-lasting benefit is also acheived by daily administration for 28 days (4 tablets per day) of this composition to a patient suffering from gastric ulcers.

Similar results are achieved with tablets formulated as above but replacing the bismuth subsalicylate with bismuth subcitrate, bismuth citrate, tripotassium dicitrato bismuthate, bismuth tartrate, or a mixture of bismuth subsalicylate and bismuth subcitrate. Similar results are also achieved with tablets formulated as above but replacing the cimetidine with ranitidine, or a mixture of cimetidine and ranitidine.

EXAMPLE II

Pharmaceutical Compositions in Capsule Form

Capsules are prepared by conventional methods, comprised as follows:

| Ingredients | Mg/Capsule |
| --- | --- |
| Bismuth subcitrate | 300 of bismuth |
| Cimetidine | 300 |
| Lactose | To fill to volume of capsule |

One of the above capsules administered orally 4 times a day for 21 days substantially reduces the symptomology of a patient afflicted with a gastric ulcer. Similar results are obtained with capsules formulated above but replacing the bismuth subcitrate with subsalicylate; or by replacing the cimetidine with ranitidine.

EXAMPLE III

Pharmaceutical Compositions in Liquid Form

A composition, according to the present invention, is made comprising:

| Component | % (by Weight) |
| --- | --- |
| bismuth subsalicylate | 1.7500 |
| cimetidine | 1.0000 |
| magnesium aluminum silicate[1] | 0.9850 |
| methyl cellulose | 1.0790 |
| FD&C Red 3 dye | 0.0104 |
| FD&C Red 40 dye | 0.0054 |
| salicylic acid | 0.0706 |
| sodium salicylate | 0.0598 |
| flavorant | 0.0881 |
| sodium saccharin | 0.0608 |
| water | Balance |

[1] Veegum; manufactured by R. T. Vanderbilt Company, Inc.

A batch composition, comprised as above, is made by first mixing the Veegum in a quantity of water, followed by addition of the methyl cellulose. The suspension system is then mixed for approximately 30 minutes. The bismuth subsalicylate and cimetidine are added, as a slurry of approximately 9% in water, and mixed for approximately 25 minutes. The FD & C Red 3 dye is then added, and the product mixed for approximately 10 minutes. The FD & C Red 40 dye is added, and mixed for approximately 12 minutes. The salicylic acid, sodium salicylate, flavorant and sodium saccharin are then added, and mixed for approximately 9 minutes. The batch product is then filled into individual bottles.

Two tablespoons of this liquid administered orally four times a day for ten days to a patient suffering from gastritis caused by *Campylobacter pyloridis* infection substantially improves the patient's condition.

EXAMPLE IV

Methods Comprising Concurrent Administration

A patient suffering from gastritis is treated according to a regimen comprising 28 days of oral administration of bismuth subsalicylate (as two tablespoons of Pepto-Bismol ®; sold by the Procter & Gamble Company) in the morning and oral administration of 400 mg of cimetidine (as 2 Tagamet ® tablets; sold by Smith Kline and French Laboratories) in the evening before bedtime. This regimen significantly improves the condition of the patient being treated. Similar results are obtained when the bismuth subsalicylate is replaced with bismuth subcitrate (DeNol; sold by Gist-Brocades N.V.).

Similarly effective treatment of a patient suffering from gastritis is achieved by the following regimens utilizing bismuth subsalicylate (supplied as Pepto-Bismol) and cimetidine (supplied as Tagamet): 21 days of daily oral administration of the two agents within about 5 minutes of each other; 21 days of daily oral administration of the two agents within about 5 minutes of each other followed by 7 days of treatment with only bismuth subsalicylate; and 7 days of treatment with bismuth subsalicylate followed by 21 days of daily oral administration of the two agents within about 5 minutes of each other.

EXAMPLE V

Methods Comprising Non-concurrent Administration

A patient suffering from gastritis is treated according to a regimen comprising 29 days of alternating daily oral dosing of bismuth subsalicylate (as 2 tablespoons of Pepto-Bismol ®; sold by the Procter & Gamble Company); and 400 mg of cimetidine (as 2 Tagamet ® tablets; sold by the Smith Kline and French Laboratories), with the treatment regimen beginning on day 1 with administration of the bismuth subsalicylate and alternating the agents daily through day 29 which is also the administration of bismuth subsalicylate. This regimen significantly improves the condition of the patient being treated.

Similarly effective treatment of a patient suffering from gastritis is achieved by the following regimens utilizing bismuth subsalicylate and cimetidine: 14 days of daily oral administration of cimetidine, followed by 14 days of daily oral administration of bismuth subsalicylate; 7 days of daily oral administration of bismuth subsalicylate, followed by 14 days of daily oral administration of cimetidine; and 7 days of daily oral administration of bismuth subsalicylate, followed by 14 days of daily oraladministration of cimetidine, followed by 7 days of daily oral administration of bismuth subsalicylate.

What is claimed is:

1. Pharmaceutical compositions useful for treating or preventing gastrointestinal disorders, said compositions comprising:
    (a) a safe and therapeutically effective amount of a bismuth-containing agent;
    (b) a safe and therapeutically effective amount of an $H_2$ receptor blocking anti-secretory agent; and
    (c) a pharmaceutically-acceptable carrier.

2. Pharmaceutical compositions useful for treating or preventing gastrointestinal disorders, according to claim 1, wherein the bismuth-containing agent is selected from the group consisting of bismuth aluminate, bismuth subcarbonate, bismuth subcitrate, bismuth citrate, tripotassium dicitrato bismuthate, bismuth subgalate, bismuth subnitrate, bismuth tartrate, bismuth subsalicylate, and mixtures thereof.

3. Pharmaceutical compositions useful for treating or preventing gastrointestinal disorders, according to claim 1, wherein the bismuth-containing agent is a campylobacter-inhibiting bismuth-containing agent.

4. Pharmaceutical compositions useful for treating or preventing gastrointestinal disorders, according to claim 3, wherein the campylobacter-inhibiting bismuth-containing agent is selected from the group consisting of bismuth subsalicylate, bismuth subcitrate, and mixtures thereof.

5. Pharmaceutical compositions useful for treating or preventing gastrointestinal disorders, according to claim 3, wherein the $H_2$ receptor blocking anti-secretory agent is selected from the group consisting of cimetidine, ranitidine, and mixtures thereof.

6. Pharmaceutical compositions useful for treating or preventing gastrointestinal disorders, said compositions comprising:
    (a) a safe and therapeutically effective amount of a bismuth-containing agent selected from the group consisting of bismuth subsalicylate, bismuth subcitrate, and mixtures thereof;
    (b) a safe and therapeutically effective amount of an $H_2$ receptor blocking anti-secretory agent selected from the group consisting of cimetidine, ranitidine, and mixtures thereof; and
    (c) a pharmaceutically-acceptable carrier.

7. Pharmaceutical compositions useful for treating or preventing gastrointestinal disorders, according to claim 6, wherein the bismuth-containing agent is bismuth subsalicylate, and the $H_2$ receptor blocking anti-secretory agent is cimetidine.

8. Pharmaceutical compositions useful for treating or preventing gastrointestinal disorders, said compositions comprising:
    (a) from about 0.1% to about 99.8% of a bismuth-containing agent;
    (b) from about 0.1% to about 99.8% of an $H_2$ receptor blocking anti-secretory agent; and
    (c) from about 0.1% to about 99.8% of a pharmaceutically-acceptable carrier.

9. Pharmaceutical compositions useful for treating or preventing gastrointestinal disorders according to claim 8, said compositions comprising:
    (a) from about 0.1% to about 99.8% of a bismuth-containing agent selected from the group consisting of bismuth subsalicylate, bismuth subcitrate, and mixtures thereof;
    (b) from about 0.1% to about 99.8% of an $H_2$ receptor blocking anti-secretory agent selected from the group consisting of cimetidine, ranitidine, and mixtures thereof; and (c) from about 0.1% to about 99.8% of a pharmaceutically-acceptable carrier.

10. Pharmaceutical compositions according to claim 8 in unit dosage form comprising from about 50 mg to about 1500 mg of bismuth.

11. Pharmaceutical compositions according to claim 9 in unit dosage form comprising from about 50 mg to about 1500 mg of bismuth.

12. Pharmaceutical compositions according to claim 10 in unit dosage form comprising from about 1 mg to about 300 mg of an $H_2$ receptor blocking anti-secretory agent.

13. Pharmaceutical compositions according to claim 9 in unit dosage form comprising from about 50 mg to about 500 mg of bismuth, and from about 1 mg to about 300 mg of ranitidine.

14. Pharmaceutical compositions according to claim 9 in unit dosage form comprising from about 50 mg to about 500 mg of bismuth, and from about 50 mg to about 300 mg of cimetidine.

15. Methods for treating or preventing gastrointestinal disorders in humans or lower animals, said methods comprising administering to a human or lower animal in need of such treatment or prevention a safe and therapeutically effective amount of a bismuth-containing agent and a safe and therapeutically effective amount of an $H_2$ receptor blocking anti-secretory agent, and wherein said methods further comprise administering a bismuth-containing agent and an $H_2$ receptor blocking anti-secretory agent within about one hour of each other.

16. A method for treating or preventing gastrointestinal disorders in humans or lower animals, according to claim 15, wherein the bismuth-containing agent and the $H_2$ receptor blocking anti-secretory agent are both administered orally.

17. Methods for treating or preventing gastrointestinal disorders in humans or lower animals, according to claim 16, wherein the bismuth-containing agent is a campylobacter-inhibiting bismuth-containing agent.

18. Methods for treating or preventing gastrointestinal disorders in humans or lower animals, according to claim 17, wherein the campylobacter-inhibiting bismuth-containing agent is selected from the group consisting of bismuth subcitrate, bismuth subsalicylate, and mixtures thereof; and wherein further the $H_2$ receptor blocking anti-secretory agent is selected from the group consisting of cimetidine, ranitidine, and mixtures thereof.

19. Methods for treating or preventing gastrointestinal disorders in humans or lower animals, according to claim 18, wherein the campylobacter-inhibiting bismuth-containing agent is bismuth subsalicylate, and the $H_2$ receptor blocking anti-secretory agent is cimetidine.

20. Methods for treating or preventing gastrointestinal disorders in humans or lower animals, said methods comprising administering to a human or lower animal in need of such treatment or prevention a safe and therapeutically effective amount of a pharmaceutical composition according to claim 1.

21. Methods for treating or preventing gastrointestinal disorders in humans or lower animals, said methods comprising administering to a human or lower animal in need of such treatment or prevention a safe and therapeutically effective amount of a pharmaceutical composition according to claim 6.

22. Methods for treating or preventing gastrointestinal disorders in humans or lower animals, said methods comprising administering to a human or lower animal in need of such treatment or prevention a safe and therapeutically effective amount of a pharmaceutical composition according to claim 7.

23. A method for treating or preventing gastrointestinal disorders in humans or lower animals, said method comprising simultaneously dosing the gastrointestinal tract of the human or lower animal in need of such treatment or prevention with safe and therapeutically effective amounts of bismuth and ranitidine.

24. A method for treating or preventing gastrointestinal disorders in humans or lower animals, said method comprising simultaneously dosing the gastrointestinal tract of the human or lower animal in need of such treatment or prevention with safe and therapeutically effective amounts of bismuth and cimetidine.

25. A method for treating ulcers of the upper gastrointestinal tract in humans or lower animals, said method comprising simultaneously treating the upper gastrointestinal tract of the human or lower animal in need of such treatment with safe and therapeutically effective amounts of bismuth and ranitidine.

26. A method for treating ulcers of the upper gastrointestinal tract in humans or lower animals, said method comprising simultaneously treating the upper gastrointestinal tract of the human or lower animal in need of such treatment with safe and therapeutically effective amounts of bismuth and cimetidine.

27. A method for treating non-ulcerative gastrointestinal disorders in humans or lower animals, said method comprising simultaneously treating the upper gastrointestinal tract of the human or lower animal in need of such treatment with safe and therapeutically effective amounts of bismuth and ranitidine.

28. A method for treating non-ulcerative gastrointestinal disorders in humans or lower animals, said method comprising simultaneously treating the upper gastrointestinal tract of the human or lower animal in need of such treatment with safe and therapeutically effective amounts of bismuth and cimetidine.

29. A method for treating *Campylobacter pyloridis* infection of the upper gastrointestinal tract in humans or lower animals, said method comprising simultaneously treating the upper gastrointestinal tract of the human or lower animal infected with *Campylobacter pyloridis* with safe and therapeutically effective amounts of bismuth and ranitidine.

30. A method for treating *Campylobacter pyloridis* infection of the upper gastrointestinal tract in humans or lower animals, said method comprising simultaneously treating the upper gastrointestinal tract of the human or lower animal infected with *Campylobacter pyloridis* with safe and therapeutically effective amounts of bismuth and cimetidine.

31. A method for treating or preventing gastrointestinal disorders in humans or lower animals, said method comprising orally administering to a human or lower animal in need of such treatment or prevention a safe and therapeutically effective amount of a unit dose composition according to claim 10.

32. A method for treating or preventing gastrointestinal disorders in humans or lower animals, said method comprising administering to a human or lower animal in need of such treatment or prevention a safe and therapeutically effective amount of a unit dose composition according to claim 11.

33. A method for treating or preventing gastrointestinal disorders in humans or lower animals, said method comprising administering to a human or lower animal in need of such treatment or prevention a safe and therapeutically effective amount of a unit dose composition according to claim 13.

34. A method for treating or preventing gastrointestinal disorders in humans or lower animals, said method comprising administering to a human or lower animal in need of such treatment or prevention a safe and therapeutically effective amount of a unit dose composition according to claim 14.

35. A method for treating or preventing gastrointestinal disorders in humans or lower animals, said method comprising simultaneously treating, for from about 1 to about 60 days, the gastrointestinal tract of the human or lower animal in need of such treatment or prevention with from about 50 mg to about 5000 mg per day of bismuth and from about 1 mg to about 10 g per day of ranitidine.

36. A method for treating or preventing gastrointestinal disorders in humans or lower animals, said method comprising simultaneously treating, for about 1 to about 60 days, the gastrointestinal tract of the human or lower animal in need of such treatment or prevention with from about 50 mg to about 5000 mg per day of bismuth and from about 50 mg to about 5000 mg per day of cimetidine.

37. Methods for treating of preventing gastrointestinal disorders in human or lower animals, said methods comprising administering to a human or lower animal in need of such treatment or prevention a safe and therapeutically effective amount of a bismuth-containing agent and a safe and therapeutically effective amount of an $H_2$ receptor blocking anti-secretory agent, and wherein said methods further comprise administering a bismuth-containing agent and an $H_2$ receptor blocking anti-secretory agent within about five minutes of each other.

* * * * *